United States Patent
Morimoto et al.

(10) Patent No.: US 11,931,234 B2
(45) Date of Patent: Mar. 19, 2024

(54) WEARABLE ARTICLE HAVING CHARACTERISTIC MATERIAL PROPERTIES

(71) Applicant: The Procter & Gamble Company, Cincinnati, OH (US)

(72) Inventors: Koichi Morimoto, Beijing (CN); Hui Liu, Beijing (CN); Xu Gao, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 1222 days.

(21) Appl. No.: 16/550,390

(22) Filed: Aug. 26, 2019

(65) Prior Publication Data

US 2019/0374399 A1 Dec. 12, 2019

Related U.S. Application Data

(63) Continuation of application No. PCT/CN2017/074990, filed on Feb. 27, 2017.

(51) Int. Cl.
  *A61F 13/15* (2006.01)
  *A61F 13/49* (2006.01)
  (Continued)

(52) U.S. Cl.
  CPC .. *A61F 13/51456* (2013.01); *A61F 13/15699* (2013.01); *A61F 13/49009* (2013.01);
  (Continued)

(58) Field of Classification Search
  CPC .......... A61F 13/15699; A61F 13/15723; A61F 13/49; A61F 13/49009; A61F 13/496;
  (Continued)

(56) References Cited

U.S. PATENT DOCUMENTS 6,797,377 B1 * 9/2004 DeLucia ............ D04H 1/43838
                                                524/447
7,901,393 B2   3/2011 Matsuda et al.
(Continued)

FOREIGN PATENT DOCUMENTS

CN         105828770 A    8/2016
EP           3326596      5/2018
(Continued)

OTHER PUBLICATIONS

International Search Report and Written Opinion, PCT/CN2017/074990, dated Nov. 23, 2017 (P&G AA1202).
(Continued)

*Primary Examiner* — Bradley H Philips
(74) *Attorney, Agent, or Firm* — Charles R. Matson

(57) ABSTRACT

Disclosed is a wearable article continuous in a longitudinal direction and a transverse direction comprising an elastic belt region, a crotch region, a waist opening and two leg openings; the elastic belt region is a laminate comprising an inner sheet made of nonwoven fiber, and an outer sheet made of nonwoven fiber, and a plurality of elastic bodies configured to stretch the elastic belt region in the transverse direction, the crotch region comprises an outer cover layer at the most garment facing side, the outer cover layer being the same material as the outer sheet; wherein the outer sheet has a Compression Work of more than about 550 gfmm, a Compression Average Rigidity of less than about 500 gf/mm$^3$, a Surface Roughness Wavelength of more than about 1.7 mm, and a Glossiness of less than about 5.3, the Compression Work, the Compression Average Rigidity, the Surface Roughness Wavelength and the Glossiness according to the measurements herein.

7 Claims, 4 Drawing Sheets

(51) Int. Cl.
*A61F 13/496* (2006.01)
*A61F 13/514* (2006.01)
*A61F 13/64* (2006.01)
*D04H 1/541* (2012.01)
*D04H 1/558* (2012.01)

(52) U.S. Cl.
CPC ............ *A61F 13/496* (2013.01); *A61F 13/64* (2013.01); *D04H 1/5412* (2020.05); *D04H 1/5414* (2020.05); *D04H 1/558* (2013.01); *A61F 13/15723* (2013.01); *A61F 2013/49063* (2013.01)

(58) Field of Classification Search
CPC .. A61F 13/514; A61F 13/51456; A61F 13/64; A61F 2013/49063
See application file for complete search history.

(56) References Cited

U.S. PATENT DOCUMENTS

| | | | |
|---|---|---|---|
| 8,298,205 B2 | 10/2012 | Norrby et al. | |
| 8,622,983 B2 | 1/2014 | Wilkes et al. | |
| 9,220,643 B2 | 12/2015 | Mariko et al. | |
| 9,333,119 B2 * | 5/2016 | Zink | B32B 5/26 |
| 9,421,134 B2 | 8/2016 | Schlinz et al. | |
| 9,549,859 B2 | 1/2017 | Wilkes et al. | |
| 2004/0102757 A1 | 5/2004 | Olson | |
| 2004/0243083 A1 | 12/2004 | Matsuda et al. | |
| 2006/0030831 A1 | 2/2006 | Matsuda et al. | |
| 2007/0287975 A1 * | 12/2007 | Fujimoto | A61F 13/496 604/396 |
| 2009/0000561 A1 * | 1/2009 | Takahashi | A01K 1/0107 119/171 |
| 2009/0326504 A1 * | 12/2009 | Kaneda | A61F 13/51458 604/385.24 |
| 2011/0160692 A1 | 6/2011 | Wilkes et al. | |
| 2014/0088542 A1 | 3/2014 | Wilkes et al. | |
| 2014/0332436 A1 | 11/2014 | Sasayama et al. | |
| 2016/0331600 A1 | 11/2016 | Polidori et al. | |
| 2017/0156945 A1 * | 6/2017 | Hashimoto | A61F 13/515 |
| 2017/0165128 A1 | 6/2017 | Morimoto et al. | |
| 2017/0189244 A1 | 7/2017 | Mueller et al. | |
| 2017/0335498 A1 | 11/2017 | Hansen et al. | |
| 2018/0168885 A1 | 6/2018 | Zink et al. | |

FOREIGN PATENT DOCUMENTS

| | | |
|---|---|---|
| JP | S63162729 A | 7/1988 |
| JP | 2004344532 A | 12/2004 |
| JP | 2016010517 A5 | 10/2016 |
| JP | 2016202942 A | 12/2016 |
| WO | WO2016168997 | 10/2016 |

OTHER PUBLICATIONS

Supplemental International Search Report and Written Opinion, PCT/CN2017/074990, dated Mar. 6, 2019 (P&G AA1202).

* cited by examiner

WEARABLE ARTICLE HAVING CHARACTERISTIC MATERIAL PROPERTIES

CROSS REFERENCE TO RELATED APPLICATION

This application is a continuation, under 35 USC 120, of Application No. PCT/CN2017/074990, filed on Feb. 27, 2017, which is herein incorporated by reference in its entirety.

FIELD OF THE INVENTION

The present invention relates to wearable articles having an elastic belt region having characteristic material properties.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult, and also for younger babies requiring a soft fit around the waist opening and leg openings.

Pant-type articles may take various structures wherein the circumference of the waist opening and vicinity thereof is made elastic enough to facilitate the wearer or the caregiver to expand the article and insert the wearer's legs into the leg openings for wearing the article. The region of the waist circumference and vicinity thereof is often referred to as the elastic belt. One type of structure for the pant-type article is the belt-type pant having a main body to cover the crotch region of the wearer and a separate elastic belt defining the waist opening and leg opening, such as described in PCT Publication WO 2006/17718A. Another type of structure for the pant-type article is the uni-body pant configured such that the outer cover of the article completely covers the entirety of the garment-facing surface of the article, wherein the portion configured to stretch about the torso is considered the elastic belt region.

Whatever the structure of the pant-type article may be, the elastic belt region may be the portion which is most touched and observed by the wearer or the caregiver upon use, and thus its properties most associated with the function and quality of the article. By function, what may be desired is an elastic belt region which is easily stretchable, and provides a comfortable yet reliable fit. By quality, what may be desired is an undergarment kind of appearance, and pleasant tactile sense such as softness and cushiony touch.

Meanwhile, from a manufacturer's point of view, there is desire to provide a high quality absorbent article while controlling cost for making the article by selecting materials and assembling them in a manner that may provide the best user experience per cost of material.

Based on the foregoing, there is a need for a wearable article having improved tactile and aesthetic sense for the elastic belt region without compromise to the wearability performance. There is further a need for providing parameters that guide the manufacturer to select materials and to assemble them in a manner that provides a favorable return of investment for manufacturing a wearable article.

SUMMARY OF THE INVENTION

The present invention is directed to a wearable article continuous in a longitudinal direction and a transverse direction comprising an elastic belt region, a crotch region, a waist opening and two leg openings;

the elastic belt region is a laminate comprising an inner sheet made of nonwoven fiber, and an outer sheet made of nonwoven fiber, and a plurality of elastic bodies configured to stretch the elastic belt region in the transverse direction, the crotch region comprises an outer cover layer at the most garment facing side, the outer cover layer being the same material as the outer sheet;

wherein the outer sheet has a Compression Work of more than about 550 gfmm, a Compression Average Rigidity of less than about 500 gf/mm$^3$, a Surface Roughness Wavelength of more than about 1.7 mm, and a Glossiness of less than about 5.3, the Compression Work, the Compression Average Rigidity, the Surface Roughness Wavelength and the Glossiness according to the measurements herein.

The present invention is also directed to a method of selecting material for making a wearable article as described above.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
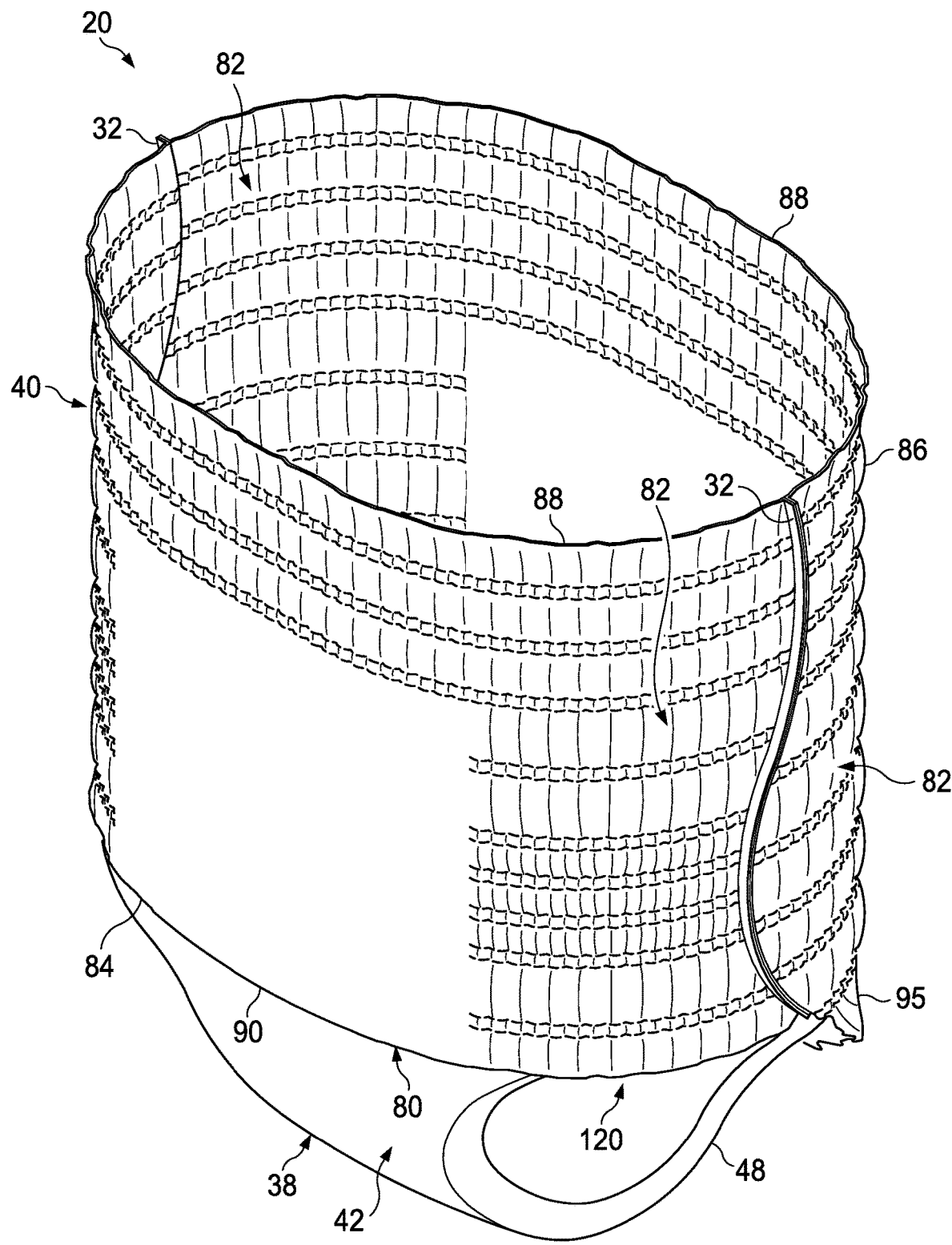
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having an L* value of at least 94, an a* value equal to 0±2, and a b* value equal to 0±2 according to the CIE L* a* b* color system.

DETAILED DESCRIPTION OF THE INVENTION

Figure 2:
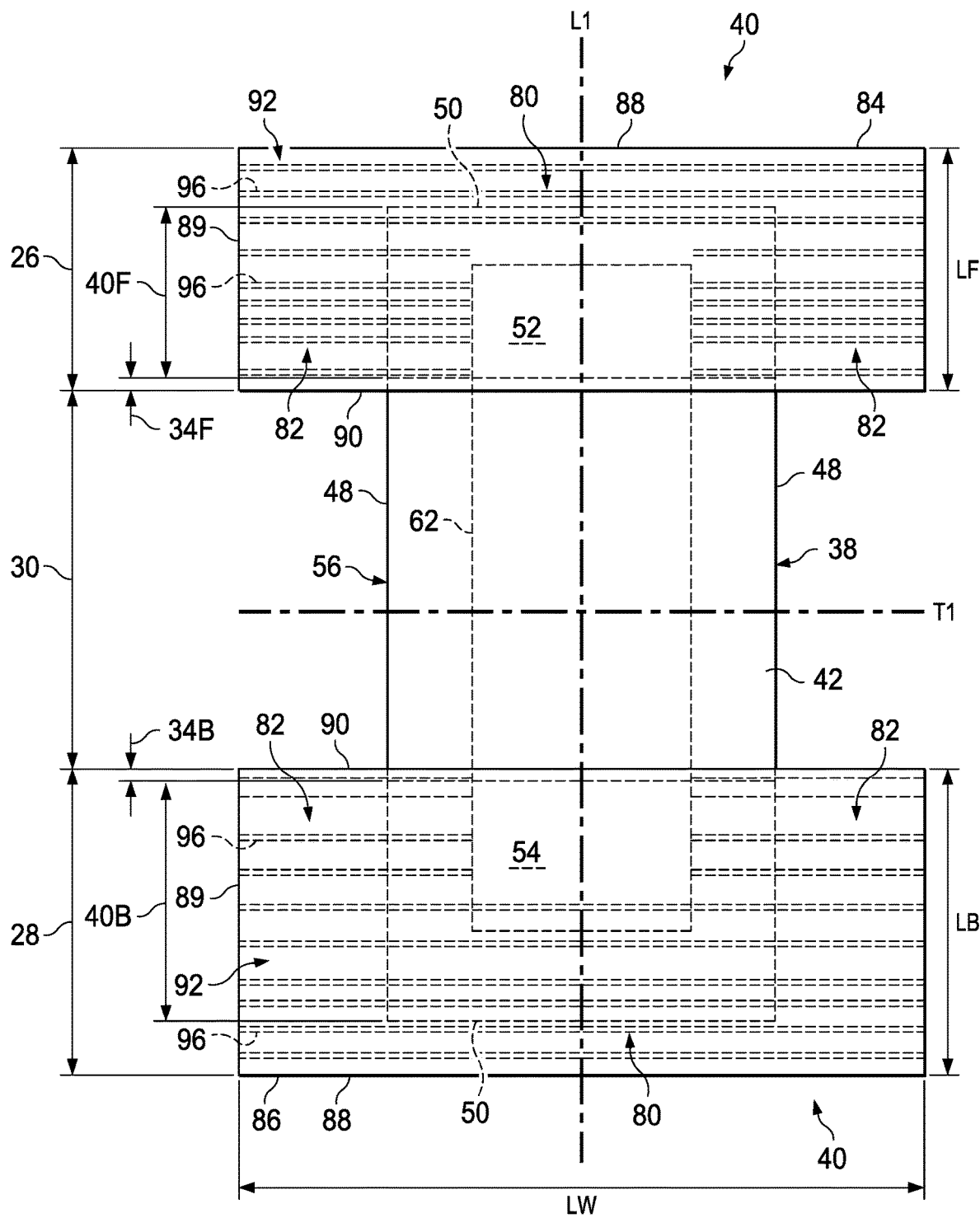
FIG. 2 is a schematic plan view of one embodiment of a wearable article of the present invention with the seams unjoined and in a flat uncontracted condition showing the garment facing surface.

FIG. 1 is a perspective view of an embodiment of the wearable article 20 of the present invention and FIG. 2 is a schematic plan view of the same article with the seams enjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a body facing surface, a garment facing surface, a front region 26, a back region 28, a crotch region 30, and seams 32 which join the front region 26 and the back region 28 to form two leg openings and a waist opening. The wearable article 20 may be a belt-type pant comprising a central chassis 38 to cover the crotch region of the wearer, a front belt 84 and a back belt 86 (hereinafter may be referred to as "front and back belts"), the front and back belts 84, 86 forming a discrete ring-like elastic belt 40 (hereinafter may be referred to as "waist belt") extending transversely defining the waist opening. For the belt-type pant, the discrete ring-like elastic belt 40 may also be referred to as the elastic belt region 40. For the belt-type pant, the front and back belts 84, 86 and the central chassis 38 jointly define the leg openings. The wearable article 20 may be a uni-body type pant wherein the central chassis 38 is continuous with the front and back belt 84, 86, wherein the leg openings are continuously formed. For the uni-body pant, the belt portion existing between the side seams are considered the elastic belt region 40, wherein the region is considered to terminate by an imaginary line running in the transverse direction between the proximal edges of the side seams. The remainder of the article except the elastic belt region 40 is considered the crotch region 30.

Figure 3:
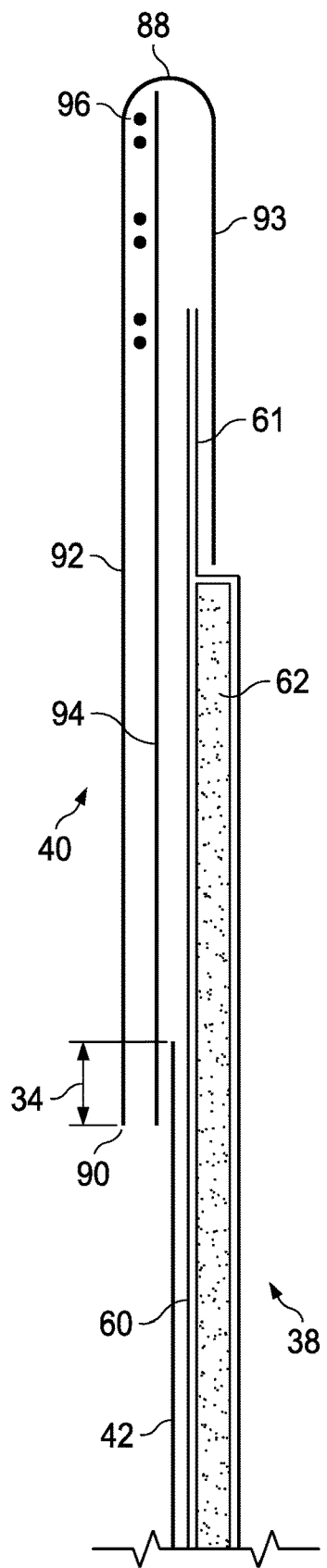
FIG. 3 is a cross section view of FIG. 2 taken along the longitudinal center line.

Referring to FIG. 3, the central chassis 38 comprises a backsheet 60 and an outer cover layer 42 for covering the garment-facing side of the backsheet 60. The backsheet 60 may be a water impermeable film. The outer cover layer 42 may be a nonwoven sheet. The central chassis 38 may contain an absorbent core 62 for absorbing and containing body exudates disposed on the central chassis 38. In the embodiment shown in FIG. 2, the central chassis 38 has a generally rectangular shape, left and right longitudinally extending side edges 48 (hereinafter may be referred to as "side edge") and front and back transversely extending end edges 50 (hereinafter may be referred to as "end edge"). The central chassis 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the central chassis 38, the center of the back belt 86 is joined to a back waist panel 54 of the central chassis 38, the front and back belts 84, 86 each having a left side panel and a right side panel 82 where the central chassis 38 does not overlap.

The elastic belt region of the article of the present invention acts to dynamically create fitment forces and to distribute the forces dynamically generated during wear. The proximal edge 90 is located closer than the distal edge 88 relative to the crotch panel 56 of the central chassis 38. The front and back belts 84, 86 may be joined with each other only at the side edges 89 at the seams 32 to form a wearable article having a waist opening and two leg openings. Each leg opening may be provided with elasticity around the perimeter of the leg opening. For the belt-type pant, the elasticity around the leg opening may be provided by the combination of elasticity from the front belt 84, the back belt 86, and any from the central chassis 38.

The transverse width of the backsheet 60 and the outer cover layer 42 may be the same, or may be varied (not shown). For example, the backsheet 60 may have a shorter transverse width compared to that of the outer cover layer 42. By such configuration, the longitudinal side edges 48 of the crotch panel 56, which make part of the leg openings, may have better breathability. Further, such configuration may provide cost saving.

The front belt 84 and back belt 86 are configured to impart elasticity to the belt 40. The front belt 84 and the back belt 86 may each be formed by a laminate comprising a plurality of elastic bodies 96 running in the transverse direction, an inner sheet 94, an outer sheet 92, and an outer sheet fold over 93 wherein the outer sheet fold over 93 is an extension of the outer sheet material formed by folding the outer sheet material at the distal edge 88 of the front and back belts; wherein the belt elastic bodies 96 are sandwiched between two of these sheets. The front belt 84 and the back belt 86 may each be made only by elastic bodies 96, the inner sheet 94, the outer sheet 92, and the outer sheet fold over 93. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made. The front and back belt 84, 86 each may have transversely continuous proximal and distal edges, the proximal edge 90 being located closer than the distal edge 88 relative to the longitudinal center of the article. The elastic bodies 96 may be disposed in the same or different denier, interval, and force between the front and back, as well as in different longitudinal positions of the belt.

The front and/or back belt 84, 86 may be treated such that certain of the area overlapping the front and/or back waist panel 52, 54 of the central chassis 38 are removed of elasticity. Removal of elasticity from a certain area of the front and/or back waist panel 52, 54 may be advantageous when the central chassis 38 comprises an absorbent core 62, in that elasticity in the front and/or back area overlapping the absorbent core 62 may cause bunching of the absorbent layer or any of the layers in the absorbent core 62 and interfere with close fit of the central chassis 38 to the wearer. In one embodiment, at least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the central chassis 38. Referring to FIG. 2, the entire area where the elastic bodies 96 overlap with the absorbent core 62 may be removed of its elasticity as in the front belt 84. Alternatively, as seen in the back belt 86, the elastic bodies 96 overlapping the absorbent material non-existing region 61 and toward the distal edges of the absorbent core 62 may be disposed in active elasticity for good fit of the central chassis 38. This may be advantageous in preventing leakage.

Referring to FIG. 2, the transverse width LW of the back belt 86 in the uncontracted condition may be the same as the transverse width of the front belt 84 of the same condition. Such an article may be economically made.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such configuration, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the central chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

The elastic belt region 40 may be closely associated with the function and quality of the article, thus materials for forming the elastic belt region 40 are carefully selected by the manufacturer for providing the desirables for the article. Soft and silky touch of the belt, and undergarment kind of appearance of the belt may be associated with high quality, and thus generally favorably accepted by the user. The user may be the wearer or the caregiver. As such, use of materials which provide the aforementioned tactile and aesthetic sense is desired. However, it requires much resources to select the materials by having to create the finally assembled article for testing its performance by the user. It would be advantageous to have a method of selecting the material by use of a set of parameters measurable of the material per se, for predicting its tactile and aesthetic acceptance when assembled as an article.

The outer sheet 92 and inner sheet 94 of the present invention may meet certain parametric requirements as detailed below. Among the parameters of interest, Compression Work (CW), Compression Average Rigidity (CAR), Surface Roughness Wavelength (SRW) and Qmax are obtained from the FTT Test methods below. Information about the FTT Test method may be found in the paper "Fibers and Polymers 2014, Vol. 15, No. 7, 1548-1559" titled "A Simultaneous Measurement Method to Characterize Touch Properties of Textile Materials" by Xiao Liao et al. Among the parameters of interest, Glossiness is obtained from the Gloss Test method below.

The outer sheet 92 may have a Compression Work (CW) of at least about 550 gfmm, or at least about 580 gfmm, or at least about 610 gfmm. CW is the total compression work provided to the material by a given force, or the amount of total deformation provided to the material by a given force. Without being bound by theory, it is believed that the higher the CW, the more work the material can receive and absorb, thus softer the perception of the elastic belt region by the user.

The outer sheet 92 may have a Compression Average Rigidity (CAR) of less than about 500 gf/mm$^3$, or less than about 480 gf/mm$^3$, or less than about 460 gf/mm$^3$. CAR is the average force needed to compress the material by 1 mm. Without being bound by theory, it is believed that the lower the CAR, the more cushiony the perception of the elastic belt region by the user. Further, while it may be intuitive that a material of low CAR should also have a low CW, this is not necessarily the case. Without being bound by theory, materials having the combination of relatively higher CW and relatively lower CAR are believed to provide cushiony, yet soft perception during the overall experience of touching the elastic belt region 40 from the outside.

The outer sheet 92 may have a Surface Roughness Wavelength (SRW) of at least about 1.7 mm, or at least about 2.0 mm, or at least about 2.3 mm. SRW is an indication of surface macro structure, namely higher SRW means coarser irregularities on the surface. Without being bound by theory, it is believed that the higher the SRW, the softer the perception of the elastic belt region by the user. Unlike CW and CAR which concern the elasticity force in the thickness direction, SRW is for measuring the frequency of surface structure in the direction along the surface of the sheet. Without being bound by theory, in that the SRW herein is measured at the magnitude of 1 mm to a few mm, the higher the SRW, the fingers perceive more flat area of the sheet and consider the sheet softer. On the other hand, the lower the SRW, the irregularities become smaller than the perceivable level of fingers, that the fingers perceive less flat area of the sheet and consider the sheet as less soft. This is counterintuitive, in that the higher the SRW, the coarser the surface structure, however, the softer the sheet is perceived.

The outer sheet 92 may have a Glossiness of less than about 5.3, or less than about 5.1, or less than 4.9. Without being bound by theory, it is believed that reduced glossiness is associated with naturalness, loft, or softness of the material by the user. Without being bound by theory, it is also believed that reduced glossiness may affect the tactile perception of the user to perceive that the material is softer.

Accordingly, by measuring the material of the 4 parameters above, one may predict if the material provides tactile and aesthetic acceptance to the user when assembled as an article. The outer sheet 92 of the present invention may have a Compression Work of at least about 550 gfmm, a Compression Average Rigidity of less than about 500 gf/mm3, a Surface Roughness Wavelength of at least about 1.7 mm, and a Glossiness of less than about 5.3.

The inner sheet 94 may have a Qmax of less than about 1650 W/m$^2$, or less than about 1585 W/m$^2$, or less than about 1520 W/m$^2$. Qmax indicates the energy transmitted during compression. Without being bound by theory, the less the Qmax, the warmer the tactile perception of the elastic belt region, thus associated with fluffy or softer touch. The property of the inner sheet 94, rather than the outer sheet 92, is considered relevant for this parameter, in that warmth of the belt elastic region is perceived when the user inserts hands into the article and stretches the article.

The inner and outer sheets 92, 94 may be the same or different material, and selected to provide characteristics such as breathability, softness, cushiony feel, loftiness, and combinations thereof, depending on the desirables of the resulting article. The inner and outer sheets 92, 94 may have the same or different basis weight, stiffness, texture or any combination thereof. The outer sheet 92 may have a higher basis weight than the inner sheet 94 for providing the favorable tactile acceptance as discussed above, while controlling cost.

The outer sheet 92 for forming the elastic belt region 40 may have a certain material thickness to provide the lofty undergarment-like appearance and feel, for example, at least about 0.25 mm, or at least about 0.3 mm. The material thickness herein is related to materials obtained from a finished product according to the "Preparation for Thickness and Basis Weight" below and measured by "Base caliper method—ASTM D 654 Standard Test Method for Thickness of Paper and Paper Board" with modification of the loading to 500 Pa. Suitable for the outer sheet 92 of the present invention include: hi-loft nonwoven, air-through carded nonwoven, and spunbond nonwoven made of crimping fiber made through core eccentric bicomponent filament or side by side bicomponent filament, preferably air-through carded nonwoven. Non-limiting examples of materials suitable for the outer sheet 92 include: 20-50 gsm air-through carded nonwoven made of less than 15 μm diameter PE/PET bi-component staple fiber, such as those with a tradename of FJ206 available from Dayuan, Beijing China.

Suitable for the inner sheet 94 of the present invention include: 10-40 gsm soft nonwoven, spunbond nonwoven with filament additive slip agent, spun high-loft nonwoven or air-through carded nonwoven, preferably spun high-loft nonwoven.

The material for the outer cover layer 42 may be selected to provide characteristics such as breathability, softness, cushiony feel, loftiness, and combinations thereof, depending on the desirables of the resulting article. The outer cover layer 42 may be made of the same material as the outer sheet 92 to provide integral aesthetic and tactile senses for the article. By "the same material", what is meant is that the nonwoven has the same type of filament in shape, composition, diameter difference of no more than 2 μm, and basis weight difference of no more than 2 gsm. Such comparison of the materials is made by analyzing the materials by SEM and FTIR measurements as detailed below. The basis weight herein is related to materials obtained from a finished product according to the "Preparation for Thickness and Basis Weight" below and measured by "Basis weight—ASTM D 756 Practice for Determination of Weight and Shape Changes of Plastics Under Accelerated Service Conditions".

Referring to FIG. 3, for the belt-type pant the front and back belts 84, 86 are discontinuous with one another in the crotch region 30, and the outer cover layer 42 is the garment-facing surface in the crotch region 30. The outer cover layer 42 may extend only partly in the longitudinal direction of the front waist panel 52 and the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability to the overall article. Further, this may provide cost saving of the outer cover layer 42 material. Accordingly, looking at the layers of elements between the garment facing surface and the backsheet of the center chassis 38 of FIG. 3, there exists a transitional region 34 disposed on the waist panel 52 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for a wearable article in an economical manner, printing may be provided on the garment facing side of the backsheet 60. By providing the transitional region 34 as short as possible, applying adhesive to the transitional region 34 to enhance transparency, or simply avoiding displaying artwork in the transitional region 34, compromised appearance of the artwork over different layers of material between the artwork and the observer may be avoided.

Alternatively, when artwork provided on the backsheet 60 extends across the elastic belt region 40 and the crotch region 30, the area of the artwork in the belt region 40 may be provided in reduced brightness and increased contrast compared to the area in the crotch region 30; such that the intensity of the artwork appear to be substantially similar when observed as an article from the garment facing side. By providing the artwork in reduced brightness and increased contrast, the artwork is less influenced by opaqueness provided by the overlaying layers of material.

Alternatively and/or additionally, the artwork in the elastic belt region 40 may be printed on the garment facing surface of the inner sheet 94 or the body facing surface of the outer sheet 92, and the artwork in the crotch region 30 may be printed on the backsheet 60. By printing the artwork in these specific layers, the number of layers between the garment facing surface and the printing may be made equal, thus the appearance difference may be alleviated. The opacity difference between the outer sheet 92 and the outer cover layer 42 may be minimized by selecting the layers to match the opacity, or by disposing the same material. The artwork for the elastic belt region 40 may be printed directly on the inner sheet 94 or the outer sheet 92 by ink, or by disposing a colored web of a predetermined shape.

As mentioned above, the front belt may have a longitudinal length of LF; and the back belt may have a longitudinal length of LB, and the outer sheet fold over 93 is formed by folding the outer sheet material at the distal edge 88 of the front and back belts. The front outer sheet fold over 93 may have a longitudinal length of at least about 0.3LF, or from about 0.3LF to about 0.7LF, or from about 0.5LF to about 0.7LF. The back outer sheet fold over may have a longitudinal length to match the length of the front outer sheet fold over. Namely, the back outer sheet fold over may have about the same length as the front outer sheet fold over.

As mentioned above, the elastic belt region 40 exhibits elasticity due to the plurality of elastic bodies 96 running in the transverse direction, wherein the elastic bodies 96 are adhered to the inner and outer sheets 92, 94. Tensile stress of the elastic belt region 40 may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. The elastic bodies may be elastic strands having a dtex of from about 470 to about 1100 and disposed at an elongation of from about 110% to about 290%. By elongation, "0% elongation" is meant the original length of the elastic body 96. Some elastics may be disposed to impart higher tensile stress in certain regions. Such one or more elastics of higher tensile stress may be disposed in an array of 2-4 elastic strands having an interval within the array of between 2-4 mm. The array may be disposed on the front belt between the longitudinal length of from about 0.5LF to about 0.85LF from the waist opening. The array may be disposed on the back belt between the longitudinal length of from about 0.25LF to about 0.5LF from the waist opening.

The articles of the present invention provide overall softness and the perception of being easy to apply, comfortable for the wearer to wear, allowing the wearer to move at ease, undergarment like, and overall high quality.

1. Fabric Touch Tester (FTT) Test and Gloss Test 1-1. Sample Preparation

To obtain a nonwoven raw material sample, lay the material flat on a bench with the technical face-side upward, and a 310 mm (along machine direction) by 110 mm (in the perpendicular direction of machine direction) rectangle shape of sample are cut using scissor. The technical face-side is the surface intended to be used as the garment-facing surface for the outer sheet 92, and the body-facing surface for the inner sheet 94.

To obtain a sample of the outer sheet 92 and the inner sheet 94 from a finished article, the elastic belt region removed of elasticity is chosen, and the outer sheet and inner sheet is separated from the other components such as belt laminated nonwoven layers, or backsheet film by techniques such as applying "Quik-Freeze®" type cold spray, or other suitable methods that do not permanently alter the properties of the nonwoven composition. The technical face-side is the surface used as the garment-facing surface for the outer sheet 92, and the body-facing surface for the inner sheet 94. The area where the elasticity of the belt elastic region is deactivated is selected for obtaining samples. For those articles having deactivated areas in the elastic belt region that are smaller than 110 mm by 110 mm, the outer cover layer 42 from the crotch region is used instead of the outer sheet. Care should be taken to prevent stretching of the nonwoven composition during the separation process, paying attention not to spray on the testing area. A 110 mm by 110 mm square shape is cut out using scissor for obtaining the sample.

Figure 4:
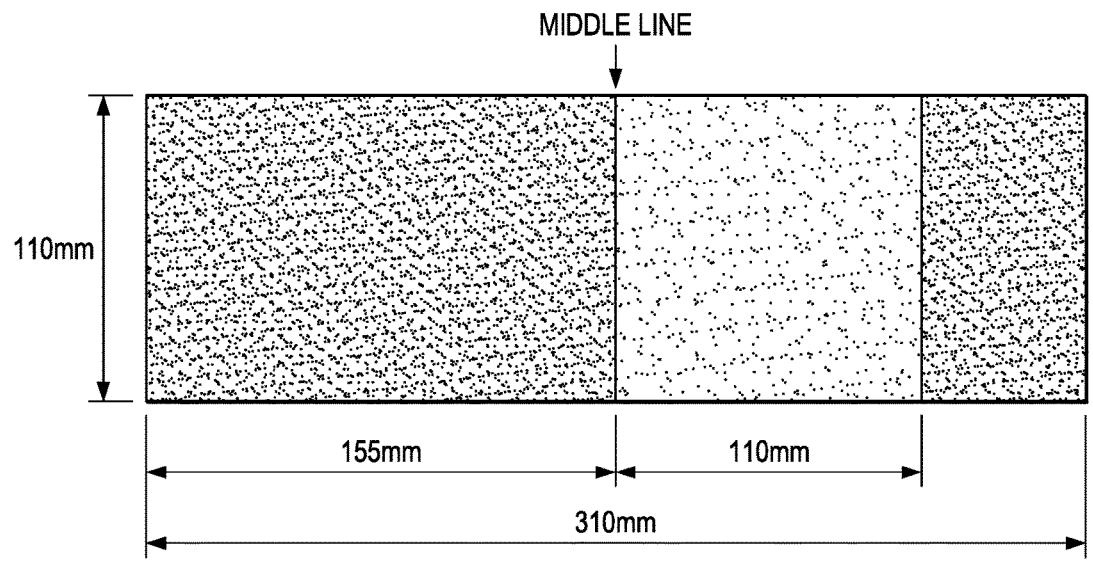
FIG. 4 is a schematic plan view of sample preparation for the Fabric Touch Test (FTT) test surface test module.

For the 110 mm by 110 mm square sample, further sample preparation is provided for the FTT Surface test. Referring to FIG. 4, attach the 110 mm by 110 mm square shape of sample on the back surface of 310 mm by 110 mm rectangle shape of a nonwoven substrate (such as 25 gsm spun-bond nonwoven material) from the middle line (155 mm distance between the front edge and middle line) by double side tape.

Five samples are cut from the same portion of identical materials, or finished products from the same package and cut out from the same area of each article, for each set of measurement. Samples are pre-conditioned in a room maintained at 23±2° C. and 50±5% relative humidity, for at least 24 hours prior to testing. Obvious wrinkles should be avoided in the tested sample, or removed before the testing.

1-2. FTT Test

The samples are measured using the Fabric Touch Tester (FTT M293) running FTT system software (available from SDL Atlas). FTT includes five modules, which may be activated at the same time and recorded of the dynamic responses from the samples, depending on the sample. They include compression, thermal, bending, friction, and surface modules. The instrument is calibrated according to the manufacturer's instructions using the standard calibration fabric provided by the vendor. All testing is performed in a room maintained at 23±2° C. and 50±5% relative humidity.

The test procedures are conducted according to the Operating Instructions for the FTT M293 manual. The sample with technical face-side upward is placed on the lower plate. For a 310 mm by 110 mm rectangle shape of sample, place the front part of the sample on the compression lower plate with the end part of the sample on the adjacent platform. The sample should be tension free with no forces exerted on any part. The FTT test is initiated with both surface testing mode and the front part of sample would be dragged downwards by the upper plate applying a continuously increasing normal force from 0-8470 gf (i.e. 0-70 gf/cm$^2$), which leads to horizontal movements of end part. The Compression and Thermal modules are measured on the front part while the Surfaces module is evaluated on the back part of the sample. For a 110 mm by 110 mm square shape of sample, put the sample on the compression lower plate for the Compression and Thermal tests. The Compression and Thermal tests are initiated with single surface testing mode and the sample would be pushed downwards by the upper plate applying a continuously increasing normal force from 0-8470 gf (i.e. 0-70 gf/cm$^2$). For the Surface test, place the front part of the additionally prepared sample (referring to FIG. 4) on the compression lower plate with the end part of the sample on the adjacent platform (the attached 110 mm by 110 mm square shape of sample towards to the surface roughness probe). The sample should be tension free with no forces exerted on any part. The Surface test is initiated with single surface testing mode and the front part of sample would be dragged downwards by the upper plate applying a continuously increasing normal force from 0-8470 gf (i.e. 0-70 gf/cm$^2$), which leads to horizontal movements of end part. The Surface module is evaluated on the end part of the sample.

Five samples are measured, and the 4 test parameters, or any subset thereof, are calculated and reported with the average value.

| Item | Module | Parameter | Symbol | Unit |
|---|---|---|---|---|
| 1 | Compression | Compression Work | CW | gf × mm |
| 2 | Compression | Compression Average Rigidity | CAR | gf × mm$^{-3}$ |
| 3 | Thermal | Thermal Maximum Flux | Qmax | W/m$^2$ |
| 4 | Surface | Surface Roughness Wavelength | SRW | mm |

1-2-1. Compression Work (CW): This parameter denotes the total work done on the sample during the compression process. Integral of the compression curve according to formula (1) is obtained wherein Da is the initial thickness at zero pressure, Dc is minimum thickness at maximum pressure, P is the measured pressure and D is the measured thickness during compression.

$$CW = \int_{D_a}^{D_c} P dD \quad (1)$$

1-2-2. Compression Average Rigidity (CAR): This parameter denotes the average force needed to compress 1 mm of sample during the middle 60% of compression process. CAR is obtained according to formula (2) wherein i to j denotes the limits of the center 60% of the compression curve and Pi and Pj are the pressure forces recorded and Di and Dj are the thicknesses recorded.

$$CAR = (P_i - P_j)/(D_j - D_i) \quad (2)$$

1-2-3. Thermal Maximum Flux (Qmax): This parameter denotes the maximum thermal flux measured according to formula (3) wherein H is the measured heat flux.

$$Q\max = \max(H) \quad (3)$$

Figure 5:
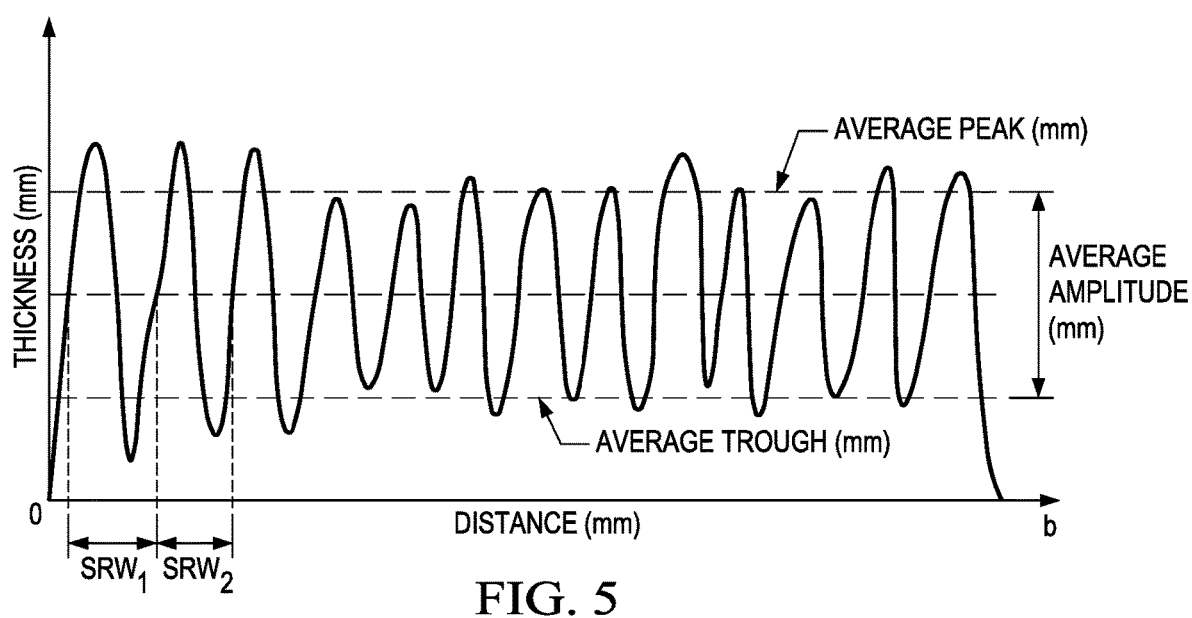
FIG. 5 is a conceptual chart of the Surface Roughness Wavelength (SRW) parameter of the present invention.

1-2-4. Surface Roughness Wavelength (SRW): This parameter denotes the average moving distance within every three intersections of the measured curve and the average line. Referring to FIG. 5, SRW is obtained according to formula (4) wherein Xpn and Xtn are distances moved when the peak and trough values are found, M is the total counts of groups of three successive intersections.

$$SRW = \frac{1}{M} \sum_{x=1}^{M} |X_{pn} - X_{tn}| \quad (4)$$

1-3. Gloss Test

Gloss is a visual impression resulting from surface evaluation. Gloss is determined using a gloss meter, such as the micro-gloss meter using a 45° illumination (available from BYK-Gardner) or equivalent. It directs a light at a specific angle to the test surface and simultaneously measures the amount of reflection.

Follow the vendor's operation for gloss measurements and calibration checks. All testing is performed in a room maintained at 23±2° C. and 50±5% relative humidity. Lay the sample flat on a bench with the face-side upward, obvious wrinkles should be removed before the testing. Put gloss meter right on the nonwoven sample. Take a reading.

Five samples are measured, analyzed with their gloss results recorded. Calculate and report the average gloss value to the nearest 0.1 gloss unit.

2. Scanning Electron Microscope (SEM) and Fourier Transform Infrared Spectroscopy (FTIR) Tests 2-1. Sample Preparation To obtain a nonwoven raw material sample, lay the material flat on a bench with the technical face-side upward, and a 20 mm (along machine direction) by 20 mm (in the perpendicular direction of machine direction) square shape of sample are cut using scissor. The technical face-side is the surface intended to be used as the garment-facing surface for the outer sheet 92 or the outer cover layer 42, and the body-facing surface for the inner sheet 94.

To obtain a sample from a finished article, the outer sheet 92 and inner sheet 94 is separated from the other components such as belt laminated nonwoven layers, or back sheet film by techniques such as applying "Quik-Freeze®" type cold spray, or other suitable methods that do not permanently alter the properties of the nonwoven composition. The technical face-side is the surface used as the garment-facing surface for the outer sheet 92 or the outer cover layer 42. The area where the elasticity of the belt elastic region is deactivated is preferred. A 20 mm by 20 mm square shape is cut out using scissors for obtaining the sample. For those articles having deactivated areas in the elastic belt region that are smaller than 20 mm by 20 mm, a 20 mm by 20 mm square shape is cut out using scissors, and the elastics are separated from the samples by techniques such as applying "Quik-Freeze®" type cold spray, or other suitable methods that do not permanently alter the properties of the nonwoven composition. Five samples are cut from the same portion of finished products from the same package for measurement.

2-2. Scanning Electron Microscope (SEM)

Scanning Electron Microscope images are taken using Hitachi TM3000 Bench-top SEM running Hitachi 3D-viewer software, or equivalent instrument. The 20 mm by 20 mm sample is submerged in liquid nitrogen and an edge is fractured with a razor blade (stainless steel coated, single edge industrial blades, 62-0165). Fractured samples are adhered to SEM mounts using double-sided Cu tape. The samples are sputter Au coated and are viewed in the SEM. The SEM images are acquired from top view, and x-section view. Fiber diameter and width measurements are made using the manual line tool in SEM operating software.

2-3. Fourier Transform Infrared Spectroscopy (FTIR)

Based on the SEM images described above, the structure of the material is observed. For samples made of mono-component fibers, all measurements are conducted by FTIR-ATR under the following conditions. A small piece (enough to cover ATR crystal) of the sample is enough to do the measurement. Apply proper and consistent pressure on top of samples using ATR pressure arm.

| | |
|---|---|
| Instrument | PerkinElmer Spotlight 400 Fourier Transform Infrared Spectroscopy, or equivalent instrument |
| Collection mode | ATR-FTIR |
| Wavenumber range | 4000-600 cm$^{-1}$ |
| Accumulation | 16 scan |
| Spectral resolution | 4 cm$^{-1}$ |

For samples made of mixed fibers or multi-component fibers such as sheath-core, side-by-side structures etc., with the aim to understand each type of fiber in the mixed fiber or each distinct part of the multi-component fiber, a few fibers are separated from each sample under the stereoscope, and are squashed up by diamond cell to be measured by Micro-IR under the following conditions. Material identification is conducted using KnowItAll informatics system, or other reference spectra library.

| | |
|---|---|
| Instrument | Nicolet iN10, or equivalent instrument |
| Wavenumber range | 4000 to 700 cm$^{-1}$ |
| Accumulation | 64 scan |
| Spectral resolution | 4 cm$^{-1}$ |

3. Preparation for Thickness and Basis Weight

The following sampling procedures are taken for measuring thickness and basis weight of a material used in a finished product.

To obtain a sample from a finished article, when available, an area free of deformation or wrinking is selected. For the belt elastic region 40, when available, area where the elasticity is deactivated is selected. The outer sheet 92, inner sheet 94, or outer cover layer 42 is separated from the other components such as belt laminated nonwoven layers, or backsheet film by techniques such as applying "Quik-Freeze®" type cold spray, or other suitable methods that do not permanently alter the properties of the nonwoven composition. The technical face-side is the surface intended to be used as the garment-facing surface for the outer sheet 92 or outer cover layer 42, and the body-facing surface for the inner sheet 94. Care should be taken to prevent stretching of the nonwoven composition during the separation process. A 100 mm by 100 mm square shape is cut out using a cutter and a 100 cm$^2$ die for obtaining the sample.

For measuring the basis weight, any remaining adhesive is removed from the sample by the following steps using Tetrahydrofuran (THF) as solvent.

1. In a hood, transfer 1 liter of THF into the 3-4 liter beaker
2. Submerge sample in the 1 liter of THF
3. Place beaker on shaking table and stir gently for 15 minutes and keep solution with sample sit for 5 additional minutes
4. Take sample out of THF solution, and carefully squeeze THF solution out of sample.
5. Let sample air dry in hood for a minimum of 15 minutes Samples are obtained from ten (10) finished products from the same package and cut out from the same area of each article, for each set of measurement. Samples are pre-conditioned in a room maintained at 23±2° C. and 50±5% relative humidity, for at least 2 hours prior to testing.

EXAMPLES

Examples 1-2 and A-C having the structure of a pant type wearable article are obtained as such, and some are subject to measurements as described above, and consumer acceptance tests described below.

Examples 1 and 2: Size 4 belt-type pant articles having the configuration of FIG. 2 and elastic profiles of Table 1 below, with the outer sheet and outer cover layer made by tradename FJ206 available from Dayuan, Beijing China (20 gsm air-through carded nonwoven with 15 μm diameter PE/PET bicomponent fiber) and the inner sheet made by tradename HY15015-MALAYSIA-V2 available from Fibertex (15 gsm PP spunbond nonwoven).

Example A

A Size 4 belt-type pant article having the same configuration as Example 1 except the outer sheet made by dual 17 gsm PE/PP bicomponent spunbond nonwoven available from Fibertex, and the outer cover layer made by 25 gsm PP spunbond nonwoven with melt additive, available from Pegas.

Example B

A Size 4 uni-body type pant article sold by the tradename of "Merries Pants" purchased in the Peoples Republic of China during October to November 2015.

Example C

A Size 4 belt-type pant article sold by the tradename of "Anerles Gold Pants" purchased in the Peoples Republic of China during October to November 2015.

TABLE 1

| | | dtex/elongation %/number of elastic bodies | |
|---|---|---|---|
| | | Example 1 | Example 2 |
| Front | 0-25% LF from waist opening | 540dtex/150%/4 | 540dtex/170%/4 |
| | 25-50% LF from | 540dtex/150%/2 | 540dtex/170%/2 |

TABLE 1-continued

| | | dtex/elongation %/number of elastic bodies | |
| --- | --- | --- | --- |
| | | Example 1 | Example 2 |
| | waist opening | 540dtex/150%/2 tummy cut | 540dtex/170%/2 tummy cut |
| | 50-85% LF from waist opening | 940dtex/210%/8 tummy cut | 940dtex/275%/8 tummy cut |
| | 85-100% LF from waist opening | 540dtex/150%/2 tummy cut | 540dtex/170%/2 tummy cut |
| Back | 0-25% LF from waist opening | 540dtex/150%/4 | 540dtex/170%/4 |
| | 25-50% LF from waist opening | 940dtex/130%/4 | 940dtex/170%/4 |
| | 50-85% LF from waist opening | 540dtex/210%/2 540dtex/210%/4 tummy cut | 540dtex/275%/2 540dtex/275%/4 tummy cut |
| | 85-100% LF from waist opening | 540dtex/210%/2 | 540dtex/275%/2 tummy cut |

(*1) tummy cut in Table 1 refers to removal of elasticity at the central area of elastic strands which overlap the central chassis 38, resulting in 66% effective length of elasticity.

TABLE 2

| | Outer Sheet | | | | |
| --- | --- | --- | --- | --- | --- |
| Example | CW (gfmm) | CAR (gf/mm$^3$) | SRW (mm) | Glossiness | Inner Sheet Qmax (W/m$^2$) |
| 1 | 610 *2) | 457 *2) | 2.33 | 4.75 *2) | 1526 |
| A | 90 | 2581 | 1.78 | 6.36 | 1526 |
| B | 504 | 608 | 2.74 | 5.44 | 1313 |
| C | 462 | 633 | 2.78 | 5.44 | 1253 |

*2) statistically significantly different than the remainder examples at 10% risk Consumer Acceptance Test 30 panelists who were caregivers of babies using Size 4 pants diapers at a frequency of minimum 3 pads per day, and having a mixture of usage experience of major brands: "Merries", "Huggies Gold" and "Pampers"; were recruited. Each panelist was given 9 test products altogether on a table. Among the 9 test products, Examples 1 and A-C were included. The panelists were asked to sort the 9 products on to the scale 1-10 on the table for each question. The rating score of 30 panelists were averaged for the report as in Table 3. (The remainder of the 9 products except Examples 1 and A-C were "Huggies Gold Pants", "Huggies Silver Pants", "Mammy Poko Pants", "Anerle Silver Pants", and "Goon Pants", all purchased in the Peoples Republic of China during October to November 2015.)

TABLE 3

| Values/Questions | 1 | A | B | C |
| --- | --- | --- | --- | --- |
| Overall liking | 8.3 | 6.7 | 8.4 | 7.4 |
| Being soft | 8.9 | 8.0 | 8.0 | 7.6 |
| Underwear like | 8.4 | 5 | 7.9 | 7.5 |

Inventive Example 1 which meets the parametric requirements of the present invention have high acceptance for "overall liking" and highest acceptance of "being soft" and "underwear like" while the other examples which do not meet the parametric requirements of the present invention are slightly to significantly inferior in consumer acceptance in at least some aspect. The parameters of the present invention provide a good predictability of consumer acceptance in view of tactile and aesthetic sense provided by the article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction, comprising:
   an elastic belt region, a crotch region, a waist opening and two leg openings;
   wherein the elastic belt region is a laminate comprising an inner sheet made of nonwoven fiber, and an outer sheet made of nonwoven fiber, and a plurality of elastic bodies configured to stretch the elastic belt region in the transverse direction, wherein the outer sheet is a 20-50 gsm air-through carded nonwoven made of crimping fiber made through core eccentric bicomponent filament or side by side bicomponent filament;
   wherein the crotch region comprises an outer cover layer at a most garment facing side, the outer cover layer being the same material as the outer sheet;
   wherein the outer sheet has a Compression Work of at least about 550 gfmm, a Compression Average Rigidity of less than about 500 gf/mm$^3$, a Surface Roughness Wavelength of at least about 1.7 mm, and a Glossiness of less than about 5.3; and
   a central chassis and a ring-like elastic belt comprising a front belt and a back belt;
   wherein a center of the front belt is joined to a front waist panel of the central chassis, a center of the back belt is joined to a back waist panel of the central chassis, and a remainder of the central chassis forms the crotch region, the front and back belt each having a left side panel and a right side panel where the central chassis does not overlap, and transverse edges of the front belt and the back belt are joined by a seam to form a waist opening and two leg openings; wherein the front belt and the back belt are discontinuous of each other in the longitudinal direction; and
   wherein the front belt and the back belt form the elastic belt region;
   wherein the central chassis comprises a backsheet attached to the wearer facing surface of the outer cover layer; wherein a longitudinal length of the outer cover layer is longer than a longitudinal length of the crotch region and shorter than a longitudinal length of the backsheet, an area on the front waist panel or the back waist panel where the outer cover layer is present defines a transitional region, and wherein the longitudinal length of the transitional region is no more than about 10 mm, and wherein adhesive is applied to the transitional region for a longitudinal length that is less than the longitudinal length of the transitional region.

2. The article of claim 1 wherein the inner sheet has a Qmax of less than about 1650 $W/m^2$ according to the measurements herein.

3. The article of claim 1 wherein the elastic body is an elastic strand having a dtex of from about 470 to about 1100 and disposed at an elongation of from about 110% to about 290%.

4. The article of claim 1 wherein the inner sheet is a 10-40 gsm spun high-loft nonwoven.

5. The article of claim 1 wherein the front and back belt each have the plurality of elastic bodies, the inner sheet, the outer sheet, and an outer sheet fold over; the front and back belt each having transversely continuous proximal and distal edges, wherein the outer sheet fold over is an extension of the outer sheet formed by folding the outer sheet at the distal edge of the front and back belts.

6. The article of claim 5 wherein the front belt has a straight and transversely running proximal and distal edges, the front belt has a longitudinal length of LF; and the back belt has a straight and transversely running proximal and distal edges, wherein the front outer sheet fold over has a longitudinal length of at least about 0.3LF, and wherein the back outer sheet fold over has about the same length as the front outer sheet fold over.

7. The article of claim 1 wherein at least some of the elastic stands are disposed in an array of 2-4 elastic strands having an interval within the array of between 2-4 mm, and wherein the array disposed on one or both of the front belt between the longitudinal length of from 0.5LF to 0.85LF and the back belt between the longitudinal length of from 0.25LF to 0.5LF from the waist opening.

* * * * *